United States Patent
Albrecht (10) Patent No.: US 12,357,744 B2
(45) Date of Patent: Jul. 15, 2025

(54) CONTROL APPARATUS FOR AN OPHTHALMIC SURGICAL SYSTEM, OPHTHALMIC SURGICAL SYSTEM AND COMPUTER PROGRAM PRODUCT

(71) Applicant: Carl Zeiss Meditec AG, Jena (DE)

(72) Inventor: Christian Albrecht, Aalen (DE)

(73) Assignee: Carl Zeiss Meditec AG, Jena (DE)

(*) Notice: Subject to any disclaimer, the term of this patent is extended or adjusted under 35 U.S.C. 154(b) by 900 days.

(21) Appl. No.: 17/027,522

(22) Filed: Sep. 21, 2020

(65) Prior Publication Data

US 2021/0085522 A1 Mar. 25, 2021

(30) Foreign Application Priority Data

Sep. 20, 2019 (DE) .................. 10 2019 125 430.2

(51) Int. Cl.
*A61M 1/00* (2006.01)
*A61B 3/11* (2006.01)
*A61F 9/007* (2006.01)

(52) U.S. Cl.
CPC .............. *A61M 1/774* (2021.05); *A61M 1/77* (2021.05); *A61M 1/772* (2021.05); *A61B 3/112* (2013.01); *A61F 9/007* (2013.01); *A61F 9/00745* (2013.01); *A61M 2210/0612* (2013.01)

(58) Field of Classification Search
CPC ........ A61M 1/774; A61M 1/77; A61M 1/772; A61M 3/0216; A61M 3/022; A61M 3/0283; A61M 2205/3303; A61M 2205/3306; A61M 2205/3334; A61M 2205/502; A61M 2210/0612; A61F 9/00745; A61F 9/007; A61F 9/00736; A61F 2009/00887; A61B 3/112; G16H 20/40
See application file for complete search history.

(56) References Cited

U.S. PATENT DOCUMENTS

| 2009/0306581 | A1 | 12/2009 | Claus |
| 2013/0237900 | A1* | 9/2013 | Hauger .................. A61M 1/77 604/22 |
| 2017/0027437 | A1* | 2/2017 | Neal ..................... A61B 3/1005 |
| 2018/0085349 | A1 | 3/2018 | Demopulos et al. |
| 2020/0107958 | A1* | 4/2020 | Wong ..................... A61M 1/77 |

FOREIGN PATENT DOCUMENTS

DE  10 2010 047 010 A1  4/2012

* cited by examiner

Primary Examiner — Kami A Bosworth
Assistant Examiner — Avery Smale
(74) Attorney, Agent, or Firm — Walter Ottesen, P.A.

(57) ABSTRACT

A control apparatus for an ophthalmic surgical system includes a receiver module which received a signal containing at least one geometric size of a pupil of an eye to be treated at least at a first time during a surgical procedure on the eye, at which fluid is supplied to and/or removed from the eye to be treated on the basis of set values of fluidic parameters of a fluidic apparatus. An evaluation unit allows the signal with the geometric sizes of the pupil to be compared to a geometric reference size of the pupil. An output module outputs an output signal of the evaluation unit, which contains information in respect of the geometric size of the pupil and/or information in respect of the above comparison to a control unit of the ophthalmic surgical system.

20 Claims, 4 Drawing Sheets

CONTROL APPARATUS FOR AN OPHTHALMIC SURGICAL SYSTEM, OPHTHALMIC SURGICAL SYSTEM AND COMPUTER PROGRAM PRODUCT

CROSS REFERENCE TO RELATED APPLICATION

This application claims priority of German patent application no. 10 2019 125 430.2, filed Sep. 20, 2019, the entire content of which is incorporated herein by reference.

FIELD OF THE INVENTION

One aspect of the invention relates to a control apparatus for an ophthalmic surgical system. A further aspect of the invention relates to an ophthalmic surgical system. A further aspect of the invention relates to a computer program product.

BACKGROUND OF THE INVENTION

Ophthalmic surgical systems with ophthalmic surgical apparatuses and methods for the control thereof are known from the prior art. They serve, in particular, to treat opacification of a lens of a living being, such as a human or animal. In medicine, such an opacification of a lens is also referred to as a cataract. Phacoemulsification is a widespread technique for treating the opacification of a lens. In this process, the opacified lens is comminuted or emulsified by means of a needle, which is mechanically vibrating in the ultrasonic range, often embodied as a hollow needle, and has a cutting tip at its front end, into constituent parts that are so small that these constituent parts can be aspirated by means of an aspiration apparatus, for example through an aspiration channel which may be provided by the needle.

In its immediate surroundings, the vibrating needle emulsifies the lens in such a way that the resulting lens particles can be aspirated through a line by means of a pump. A flushing fluid (irrigation fluid) is fed during this process, with the aspiration of the particles and of the fluid taking place through an aspiration line. When the lens has been completely emulsified and removed, a new artificial lens can be inserted into the empty capsular bag, and so a patient treated in this way can re-attain good vision.

Several hundred thousand operations of this type are carried out each year in Germany alone, with such a procedure being accompanied by a relatively low complication rate. However, such an operation still requires the treating surgeon to have a lot of experience. Although the vibrating needle can comminute a lens quite reliably into small particles, these particles have different sizes. If the particle is smaller than the internal diameter of an aspiration line, which usually extends within the vibrating needle, such a small particle can be aspirated together with the associated fluid without problems. However, should the particle be larger than the smallest internal diameter of the aspiration line, it cannot enter the line or blocks the latter. The state of a blocked line is referred to as occlusion. Occlusion results in a pronounced negative pressure in the aspiration line. Should the particle break into smaller parts, for example on account of a stronger vibration of the needle, such that the occlusion breaks up, strong suction arises in the region of the needle tip. In the process, a wall of the capsular bag of the lens can be aspirated to the needle tip and punctured by the needle. If the capsular bag is punctured, this leads to considerable complications for the patient, which complications must be absolutely avoided. Consequently, the treating surgeon requires full attention during the operation to avoid damage to the patient's eye. However, an operation takes a relatively long period of time if the work has to be carried out that carefully. Moreover, the breaking of an occlusion has an effect not only on the aspiration line but also on the irrigation line. Strong pressure variations may also arise there if a blockage in the aspiration line suddenly breaks up.

The pressure in the aspiration line or irrigation line changes at the onset of an occlusion or when an occlusion breaks. This can be determined using a pressure measuring device, which is coupled to the irrigation line or the aspiration line. Disadvantageously here, a relatively long time passes until a pressure change in the eye is captured by a pressure measuring device outside of the eye, that is, for example, in a console of an ophthalmic surgical system. This means that only relatively sluggish open-loop or closed-loop control of the pressure or of the volumetric flow in the aspiration line and/or irrigation line is possible, and so injury to the patient's eye cannot be avoided despite the surgeon taking great care.

The invention in US 2013/0237900 starts with the idea of capturing the consequences of a pressure change at the onset of an occlusion or when an occlusion breaks directly in the eye. Consequently, it is not necessary to ascertain a change of a surgical parameter outside of the eye. If a capturing apparatus captures the volume of an anterior chamber of the eye at a first time and a second time, it is possible, for example, to calculate the difference between the volume present at the first time and the volume present at the second time. If the absolute value of the difference is not equal to zero, this indirectly provides information about a pressure change in the anterior chamber of the eye, without a pressure needing to be measured. Consequently, a significantly changing volume of the anterior chamber of the eye can be evaluated in such a way that surgical parameters or control variables which help prevent an injury to a patient's eye are influenced. The surgeon's greatest attention therefore no longer needs to be directed to minimizing the consequences of a sudden break of an occlusion. Should an occlusion occur, the control unit of the ophthalmic surgical system can be controlled in such a way on the basis of the volume measurement at the first time and the second time that there no longer is such a strong pressure change in the aspiration line when the occlusion breaks. Since an electronic controller can carry this out more quickly and efficiently than, for example, manual control of a parameter by means of a foot pedal, phacoemulsification can be carried out within a shorter period of time and in a safer fashion by means of the control apparatus set forth therein.

Moreover, US 2009/0306581 A1 has disclosed an apparatus used to control fluidic parameters of the ophthalmic surgical system during phacoemulsification. A surgical event is recognized on the basis of image data. In particular, a capsular bag, in particular its state, can be detected in this context. Then, fluidic parameters can be set on the basis thereof.

Detecting the capsular bag is very complex and difficult on account of its three-dimensional form and partly concealed position relatively far in the interior of the eye. In particular, it also requires a very complicated optical capturing apparatus, such as an OCT system, which is also very expensive as a result thereof.

SUMMARY OF THE INVENTION

It is an object of the invention to develop a control apparatus and an ophthalmic surgical system, in each of which the setting of fluidic parameters is improved in the view of at least a reduction of fluctuations in the anterior chamber in an eye on account of an occlusion or a breakthrough of an occlusion.

One aspect of the invention relates to a control apparatus for an ophthalmic surgical system. The control apparatus includes:
- a receiver module which allows a signal to be received, the latter containing at least one geometric size of a pupil of an eye to be treated at least at one first time during a surgical procedure on the eye, at which fluid is or has been supplied to and/or removed from the eye to be treated on the basis of set values of fluidic parameters of a fluidic apparatus of the ophthalmic surgical system,
- an evaluation unit which allows the signal with the geometric size of the pupil which was captured at the first time during the surgical procedure on the eye to be compared to a geometric reference size of the pupil;
- an output module which allows the output of an output signal of the evaluation unit, which contains information in respect of the geometric size of the pupil and/or information in respect of the comparison of the captured geometric size of the pupil with the reference size of the pupil, in particular allows the output thereof to a control unit of the ophthalmic surgical system and/or allows the output thereof on an output unit, in particular of the ophthalmic surgical system, for a user.

This facilitates improved control of the fluidic settings during a surgical procedure. In particular, this also allows complications during the surgical procedure to be better avoided, particularly in the case where an occlusion breaks. The analysis of the geometric size of the pupil in particular provides a very advantageous indication in respect of the state present in the eye, in particular in the anterior chamber of the eye.

In particular, the control apparatus comprises a control unit by means of which, during the surgical procedure, in particular phacoemulsification, of the eye to be treated, at least one pressure and/or a volumetric flow, in particular in an irrigation line of an irrigation apparatus and/or in an aspiration line of an aspiration apparatus, of a fluid of the fluidic apparatus is adjustable on the basis of the output signal of the output module and/or the value of the pressure and/or the value of the volumetric flow is providable, more particularly provided, on the output unit, in particular of the ophthalmic surgical system, for a user.

One aspect of the invention, in particular a further independent aspect of the invention, relates to a control apparatus for an ophthalmic surgical system. This control apparatus has a receiver module. The receiver module allows at least one signal to be received, the latter containing at least one geometric size of a pupil of an eye to be treated at a first preparation time, at which fluid is or has been supplied to and/or removed from the eye to be treated on the basis of first set values of fluidic parameters of the fluidic apparatus of the ophthalmic surgical system during a preparation phase prior to surgical procedure. Furthermore, the receiver module allows at least one further signal to be received, the latter containing at least this geometric size of the pupil of the eye to be treated at least at one second preparation time, following the first preparation time, during the preparation phase prior to which an artificial occlusion was produced in the eye and/or prior to which an artificial break of an occlusion in the eye was produced. The control apparatus comprises the evaluation unit by means of which the signals with the geometric sizes of the pupil that occurred at the two preparation times can be evaluated.

Moreover, the control apparatus comprises the control unit which renders adjustable at least one pressure and/or volumetric flow of a fluid, in particular in an irrigation line and/or in an aspiration line, of the fluidic apparatus, in particular on the basis of the evaluated geometric sizes of the pupil, during a subsequent surgical procedure, in particular during subsequent phacoemulsification, of the eye to be treated. In addition or as an alternative thereto, provision can be made for the value of this pressure and/or the value of this volumetric flow to be providable or provided by the control apparatus on an output unit, in particular of the ophthalmic surgical system, for a user.

Consequently, the proposed control apparatus now also renders it possible to analyze the size of a pupil of the eye to be treated at least at two different preparation times during a preparation phase and assess a fluidic parameter setting underlying this on the basis of the geometric sizes. Consequently, it is possible to identify a direct correlation between the geometric size of the pupil and these fluidic parameters. This facilitates very specific output data which allow better setting of a pressure and/or a volumetric flow of the fluid of the fluidic apparatus for the phacoemulsification to be actually carried out thereafter.

This analysis is carried out during a preparation phase, in particular. The eye is already connected to the fluidic apparatus during this phase. In particular, the pupil of the eye has already been dilated by a medicament administered to the eye. However, an ophthalmic viscoelastic device (OVD) has not yet been supplied to the eye, in particular. Capsulorhexis has likewise not yet been implemented. Likewise, no ultrasonic signal acts on the eye, in particular the lens, yet.

Consequently, these fluidic parameter values set at least at the first preparation time are fluidic defaults, which are tested during the preparation phase. These tests are carried out on the real eye, in particular, which is only actually treated thereafter. During this preparation phase, different values of fluidic parameters can be set and tested accordingly at a plurality of preparation times. Then, a plurality of signals in respect of corresponding geometric sizes can be transmitted to the receiver module, also successively in time, and be evaluated by the evaluation unit.

Preferably, provision is made for a state similar to a break of an occlusion to be artificially set in the eye during this preparation phase at a third preparation time that precedes the second preparation time. As a result, such a critical state can be simulated, as it were. Hence, this allows fluid parameter settings to be tested at the second preparation time and makes it possible to find out which settings prevent an unwanted movement of the lens in the eye in the case of such a break of the occlusion. Consequently, it is possible to observe which fluidic parameter settings allow the aforementioned disadvantages in respect of the potential injury to the eye in the case of a break of the occlusion during the actual surgical procedure to at least be reduced.

In particular, the second preparation time follows the third preparation time within a short time interval. The time interval is preferably between greater than 0 ms and 1 s. More preferably, the time interval is between greater than 0 ms and 200 ms. In particular, this also means that the influence of a break of the occlusion on the pupil is preferably determined within 200 ms after the break.

In particular, different fluidic parameter settings can also be tested during the preparation phase in respect of the suitability in the case of a real break of an occlusion and/or in the case of a real occlusion on the basis of an artificially produced occlusion and/or an artificially produced break of the occlusion. In particular, these artificially produced fluid flow change states are occlusion-like states in comparison with the real occlusion or are occlusion breaking-like states in comparison with the real break.

By way of example, these can be produced artificially and in defined fashion, in particular defined in time, by a switchable valve in the aspiration line, in particular a magnetic valve.

A hollow needle has been pierced into the eye during the preparation phase. However, the hollow needle has not yet been brought so close to the capsular bag and the lens contained therein that unwanted contact with the capsular bag, in particular the back capsular bag wall, and the lens would occur if an artificial occlusion and/or an artificial break is produced. Consequently, the artificially produced states of the occlusion and/or break of the occlusion within this preparation phase are non-critical in view of the impairments specified at the outset, as may occur during the actual surgical procedure. During the preparation phase, a fluid can be supplied to the eye and/or removed from the eye via an irrigation line. In particular, this is implemented via the surgical handpiece with the hollow needle of the ophthalmic surgical system.

In addition or as an alternative thereto, decision information for a selection of a physical operation component during the subsequent operation of the eye to be treated is also providable on the basis of these geometrical sizes of the pupil evaluated by the evaluation unit.

Thus, advantageously provision is made for such a change in the geometric size of the pupil to also be deliberately provoked during such a preparation scenario in order, on the basis thereof, to be able to understand the reaction of the patient's eye to be treated. This is a very advantageous procedure to be able to simulate a potential occlusion and/or a potential break of such an occlusion during phacoemulsification by way of the set fluidic parameters and to be able to identify how the patient's eye to be treated actually reacts. As a result, information as to how the eye to be treated in the present case will react in the case of a potential real occlusion and a potential real break of such an occlusion during the actual phacoemulsification can be gleaned independently of the actual phacoemulsification. These discoveries are essential and particularly advantageous in order to be able to obtain, on the basis of this preparation scenario, the best possible settings of the operating state of the fluidic apparatus for the subsequent actual phacoemulsification. What this also achieves is that impairments as specified above and as may occur during phacoemulsification are at least reduced. This is because, in this context, the fluidic apparatus is already adapted to the best possible extent in view of its mode of operation to the individual eye to be treated. As a result, fluctuations of the anterior chamber of the eye can be better controlled and at least significantly attenuated during phacoemulsification.

Precisely this parameter of the geometric size of the pupil of an eye to be treated was found to be particularly advantageous and found to be an exact indicator for an upcoming or actual occlusion and/or an upcoming break of such an occlusion and/or an actual break of such an occlusion. Surprisingly, it was recognized that the lens with the capsular bag exhibits a specific movement behavior in the case of a pressure change in the eye, which is produced by irrigation fluid supplied to the eye and/or produced by the removal of fluid from the eye via an aspiration line. Thus, in this context, this lens is arranged in a specific normal relative position in the eye in a stable state, where normal pressure is present in the eye. In this normal state, there is no action on the eye, for example by a hollow needle of a handpiece of the ophthalmic surgical system already penetrated into the eye, and/or as a result of a supply of fluid via an irrigation line and/or as a result of an aspiration of fluid from the eye through the aspiration line.

This should be distinguished from an influence state in which, as already described above, a hollow needle of a handpiece of the ophthalmic surgical system, for example, has already been pierced into the eye or is being pierced into the eye and fluid is supplied or has been supplied to the eye via an irrigation line and/or fluid is aspirated or has been aspirated from the eye through the aspiration line. It was found that the geometric size of the pupil has changed in the influence state in comparison with the normal state. In particular, the geometric size is bigger in the influence state than in the normal state.

In particular, the geometric size of the pupil in the influence state is considered to be a reference for the proposed control apparatus. In particular, the lens in the eye has a relative reference position in this influence state. The relative reference position is such that it is situated slightly further away from the cornea of the eye than in the normal state.

If the pressure in the eye is now increased, in particular via the irrigation line, it was surprisingly found that the lens is specifically moved out of this relative reference position and moves into the interior of the eye, away from the iris and consequently also away from the cornea. The pupil was found to dilate in this state of increased pressure in the eye. Consequently, this is a clear indication that such an increase in the pupil occurs in the case of an imminent or actual occlusion. Moreover, it was surprisingly determined that the lens moves back in the direction of the relative reference position when such an occlusion breaks. Here, there may even be an approach in the direction of the cornea beyond the relative reference position. As it were, the lens swings beyond the relative reference position in these situations. The inventor has recognized that the geometric size of the pupil once again changes directly after or just after the break; specifically, it reduces significantly. In particular, it can also be reduced in relation to the size in the stable relative position or the relative reference position. Moreover, a relationship between the geometric size of the pupil and/or the change of the geometric size of the pupil and an occlusion and/or a break of an occlusion has been discovered surprisingly, yet with high precision. These discoveries form the basis of the present invention.

Precisely this parameter of the geometric size of the pupil allows a precise statement to be made during the preparation phase that precedes the actual surgical procedure, in particular the phacoemulsification, in respect of how the eye to be treated will react during the subsequent actual phacoemulsification. Consequently, various settings of values of the fluidic parameters can be tested during the preparation phase and a check can be carried out in respect of the movement of the lens in the eye following an artificial break and consequently whether the preset values of the fluidic parameters prevent an overshoot of the lens beyond the relative reference position toward the cornea. Fluidic parameter settings that prevent such an overshoot or result in only a minor overshoot are referred to as reference fluidic parameter settings. This can be evaluated by the signals which contain the geometric sizes of the pupils at the respective times.

In particular, the control apparatus comprises the evaluation unit by means of which at least one reference fluidic parameter setting during the preparation phase can be determined on the basis of the geometric sizes of the pupil captured at the two preparation times. In particular, it is possible to determine a reference fluidic parameter setting which is able to be set, in particular automatically by the control unit, in the case of a break of an occlusion during the surgical procedure.

Preferably, the control apparatus comprises the evaluation unit by means of which the reference size of the pupil can be predetermined during a preparation phase prior to the surgical procedure. In particular, the geometric size of the pupil formed at the first preparation time can be predetermined as a reference size. However, it is also possible to predetermine other geometric sizes, for example deviating by at most 10% therefrom in terms of size, as a reference size. Likewise, a geometric size of the pupil formed between the first preparation time and an occlusion can also be predetermined as a reference size. In particular, the size of the pupil occurring in the case of an artificially produced occlusion can also be predetermined as a reference size.

Preferably, at least that signal that has the smallest value of the geometric size following the artificially produced break can be evaluated by the evaluation unit. This is because if a lens moves forward in the direction of the cornea starting from the relative position in the eye assumed during the occlusion should the break of the occlusion be produced artificially, the value of the geometric size of the pupil reduces during this movement. Thus, the smallest value of the geometric size of the pupil is obtained when the lens reaches the position closest to the cornea during this movement following a break of the occlusion. In particular, this value of the geometric position, and hence of this relative position of the lens, is the value considered at the second preparation time. At least this signal produced in this respect at that point can be received by the receiver module, for example.

In particular, any signal containing a geometric size of the pupil at a plurality of preparation times, in particular many preparation times, following the break of the occlusion can be received by the receiver module. All signals produced with the start of the break of the occlusion up to the standstill of the movement of the lens and the capsular bag are received. Consequently, it is possible to receive all signals which occurred in the time interval between the break of the occlusion and the standstill of the lens and the capsular bag, the signals having the geometric sizes of the pupil arising in the process. These could be individual images or a video. In particular, the receiver module and/or the evaluation unit can be used to evaluate this plurality of signals in terms of which has the smallest value of the geometric size of the pupil. This then is the signal at the second time, which can be provided for the evaluation unit.

Provision can be made for a simulated or artificially produced occlusion and/or a break of such an occlusion to be implemented during this preparation phase, for example by switching a magnetic valve arranged in the aspiration line. This also allows an occlusion or a break of an occlusion to be artificially produced during this preparation phase.

In an advantageous embodiment, provision is made for the geometric size of the pupil to be an area and/or change in area of the pupil, and/or a diameter and/or a change in diameter of the pupil and/or a circumference of the pupil and/or change in circumference of the pupil.

In an advantageous embodiment, provision is made for a basic setting of values of the fluidic parameters to be carried out at the first preparation time. To this end, the hollow needle of the handpiece has already been pierced into the eye. No occlusion or break of an occlusion is artificially produced in this basic setting.

In particular, a ratio of the geometric sizes of the pupil can be formed by means of the evaluation unit. As a result, an actual ratio can be determined using the evaluation unit. The actual ratio can be compared to an intended ratio by means of the evaluation unit. On the basis of the comparison, the evaluation unit is able to assess whether the fluidic parameter setting preset at the first preparation time allows setting of a specific position setting of the lens in the eye toward a relative reference position, which was specified by the fluidic parameter setting at the first preparation time, in particular following a break of the occlusion, wherein this position setting, starting from the relative position of the lens at the time of the occlusion prior to the break of the occlusion, to the relative reference position is implemented without an overshoot or without overshoot beyond this relative reference position that is greater than a tolerance value. As a result, precisely the advantageous fluidic parameter settings that lead the lens, starting from its relative position in the case of an occlusion, as it were directly and without overshoot beyond the relative reference position to this relative reference position can be found out on an individual basis for the eye to be treated in the preparation phase. Thus, the movement toward the relative reference position is, as it were, damped by the advantageous fluidic parameter settings in such a way that this overshoot does not occur or only occurs to a small extent.

In particular, a ratio of the geometric sizes is thus formed. Depending on the value of the ratio, it is consequently possible to make a statement about the set fluidic parameters, in particular the fluidic parameters set at the second preparation time. This is because if the ratio of the geometric size at the first time to the geometric size at the second preparation time is greater than 1, the geometric size of the pupil at the second preparation time has significantly reduced in comparison with the first preparation time. On account of the discoveries presented above, this means that there has been a relatively significant movement of the lens in the eye, in particular beyond the relative reference position toward the cornea, following the break of the occlusion. In this example, the values of the fluidic parameters at the first time should be assessed as less suitable, where applicable. The aforementioned ratio becomes ever more advantageous, the closer the value of the ratio comes to a value of 1. This is because this means that there has been practically no change in the geometric sizes and the size is practically the same as at the two preparation times. In turn, this means that the lens in the eye practically does not move beyond the relative reference position toward the cornea on account of the values of the fluidic parameters advantageously set at the second time, even in the case of a break of the occlusion.

In particular, the fluidic parameter setting at the first preparation time can be assessed as suitable by the evaluation unit if the actual ratio is 1.

In particular, the fluidic parameter setting that was set at the first preparation time can be stored by the evaluation unit if the actual ratio equals or substantially equals the intended ratio. In particular, using the evaluation unit, the fluidic parameter setting set at the first time can be plotted in a diagram, in which a first fluidic parameter is plotted on the vertical axis and a second fluidic parameter is plotted on the horizontal axis, as a characteristic point of a characteristic line to be produced when the actual ratio equals or substantially equals the intended ratio.

In particular, provision can be made for a characteristic line to be plotted in a diagram, the characteristic line characterizing those fluidic parameter settings where the ratio of the geometric sizes of the pupil at the two times equals 1 or substantially equals 1. The region below the characteristic line can then be considered to be a non-critical value pair range for the fluidic parameters. This means that these value pairs are advantageous, particularly when an occlusion breaks, in order to avoid significant movements of the lens in the eye that overshoot the relative reference position toward the cornea. These settings can be referred to as reference fluidic parameter settings. In this context, the region above the characteristic line can then be recognized as a critical region.

Consequently, there can be an individual analysis for each eye during the preparation phase, to define what settings of fluidic parameters are advantageous in order, particularly at least in the case of a real break of an occlusion during the surgical procedure on the eye, to prevent an overshooting movement of the lens in the eye in this respect.

In particular, a 2-dimensional diagram is produced. In particular, the fluidic parameters are plotted in the diagram, in particular the pressure in the aspiration line on one axis and the pressure in the irrigation line or a parameter characterizing the pressure in the irrigation line on the other axis.

By analyzing the potential occlusion during the preparation phase, it is also possible to obtain reference fluidic parameter settings which advantageously facilitate a very quick response in the case of an actual occlusion during the subsequent surgical procedure on the eye. In particular, the ratio of the geometric size of the pupil to the geometric size of the pupil in the case of an artificially generated occlusion can be analyzed to this end. This can also be achieved by feeding signals to the receiver module and by evaluating the signals by way of the evaluation unit.

In order to assess suitable fluidic parameter settings in the case of an artificially produced occlusion during the preparation phase, it is also possible to base the evaluation on a geometric size of a different eye part of the eye, differing from the pupil, in addition to or instead of the evaluation of the geometric size of the pupil. By way of example, the limbus could be such an eye part.

Preferably, a control apparatus is embodied to comprise:
the receiver module which allows a signal to be received, the latter containing at least one geometric size of a further eye part of the eye, differing from the pupil, of the eye to be treated at the first time during the surgical procedure on the eye, at which fluid is or has been supplied to and/or removed from the eye to be treated on the basis of set values of fluidic parameters of a fluidic apparatus of the ophthalmic surgical system,
the evaluation unit which allows the signal with the geometric size of the eye part which was captured at the first time during the surgical procedure on the eye to be compared to a geometric reference size of the eye part;
the output module which allows the output of an output signal of the evaluation unit, which contains information in respect of the geometric size of the eye part and/or information in respect of the comparison of the captured geometric size of the eye part with the reference size of the eye part, in particular allows the output thereof to a control unit of the ophthalmic surgical system and/or allows the output thereof on an output unit, in particular of the ophthalmic surgical system, for a user.

In particular, the control apparatus comprises:
the receiver module which allows a signal to be received, the latter containing at least one geometric size of the eye part of the eye to be treated at least at one first preparation time, at which fluid is or has been supplied to and/or removed from the eye to be treated on the basis of first set values of fluidic parameters of a fluidic apparatus of the ophthalmic surgical system during a preparation phase prior to surgical procedure, and which allows a further signal to be received, the latter containing at least this geometric size of the eye part of the eye to be treated at least at one second preparation time, following the first preparation time, during the preparation phase prior to which an artificial occlusion was produced in the eye and/or prior to which an artificial break of an occlusion in the eye was produced,
the evaluation unit by means of which the signals with the geometric sizes of the eye part captured at the two preparation times can be evaluated.

In particular, a first evaluated geometric size of the pupil can be an increase in the geometric size of the pupil in comparison with a reference of the geometric size of the pupil in the stable state of the eye. In particular, a second evaluated geometric size of the pupil can be a reduction of the geometric size of the pupil in comparison with a reference of the geometric size of the pupil and/or a reduction in the geometric size of the pupil in comparison with a geometric size of the pupil that has been increased in relation to the reference of the geometric size of the pupil. Using this, it is possible to capture not only the actual size of the pupil but also ratios in this respect of these geometric sizes and consequently also changes in these geometric sizes when values of the fluidic parameters change. These changes in size, in particular, can be identified very accurately by optical means. On account of the above-described relationships between the sizes of the pupil and different fluidic parameter settings, it is also possible to obtain accurate settings of the pressure and/or the volumetric flow for the subsequent phacoemulsification.

In particular, one fluidic parameter is the pressure in the aspiration line. The pressure in the irrigation line can be a further fluidic parameter.

The control apparatus can be embodied with the control unit which renders adjustable at least one pressure and/or a volumetric flow, in particular in an irrigation line of an irrigation apparatus and/or in an aspiration line of an aspiration apparatus, of a fluid of the fluidic apparatus, on the basis of the evaluated geometric sizes of the eye part, during the subsequent surgical procedure, in particular during the subsequent phacoemulsification, of the eye to be treated. In addition or as an alternative thereto, the value of the pressure and/or the value of the volumetric flow is providable or provided on an output unit, in particular of the ophthalmic surgical system, for a user.

Consequently, it is not only a geometric size of the pupil of the eye to be treated but also at least one further geometric size of an eye part, differing from the pupil, that is optically captured in such an advantageous embodiment and the dependence of this geometric size of the further eye part on the respectively set values of the fluidic parameters is evaluated. Using this, it is possible to obtain even more precise information about the behavior of the eye to be treated, during this preparation phase prior to the phacoemulsification.

In an advantageous embodiment, provision is made for the further eye part to be the limbal ring and/or the cornea and/or the sclera and/or the capsular bag of the eye to be treated. The geometric size of the further eye part can be the area and/or a change in the area and/or a diameter and/or a change in the diameter. In particular, this size can also be two-dimensional, as already explained above in an advantageous embodiment in relation to the geometric size of the pupil.

In particular, decision information for a selection of a physical operation component during the subsequent phacoemulsification of the eye to be treated can also be provided on the basis of these evaluated geometric sizes of a further eye part of the eye to be treated as an alternative or in addition to what was stated above.

In particular, provision is made for the control apparatus to comprise a display unit, on which the first values of the fluidic parameters and/or the geometric sizes captured by the optical capturing apparatus and/or the geometric sizes evaluated by the evaluation unit are displayed.

Advantageously, the evaluation unit allows geometric sizes of the pupil, which are no further apart than 500 ms in time, to be compared to one another.

Using this, information can be correspondingly presented to the medical staff in a comprehensive and clearly understandable manner. The required courses of action, needed during subsequent phacoemulsification, may already be better adapted in advance and a course of action during the phacoemulsification subsequently carried out can be more precise.

The control apparatus can be a constituent part of an optical capturing apparatus. The optical capturing apparatus can be a microscope. It can also be a camera.

The control apparatus can be a constituent part of an ophthalmic surgical system. In particular, it can be external to an optical capturing apparatus, which may also be a constituent part of the ophthalmic surgical system.

A further aspect of the invention relates to an ophthalmic surgical system comprising a control apparatus as per the aforementioned aspect or an advantageous embodiment thereof. A further aspect of the invention relates to an ophthalmic surgical system comprising an optical capturing apparatus as per the aforementioned aspect or an advantageous embodiment thereof.

A further aspect of the invention relates to a computer program product comprising commands which, when the program is executed by a computer, prompt the latter to carry out a method for controlling a fluidic apparatus of an ophthalmic surgical system including the following steps:
  setting fluidic parameters of a fluidic apparatus of the ophthalmic surgical system and supplying fluid to an eye on the basis of the fluidic parameters set at a first time during a surgical procedure on the eye;
  providing a signal with a geometric size of a pupil of the eye to be treated, during and/or after the supply of the fluid and/or removal of the fluid, on the basis of the first fluidic parameters, to a receiver module of the ophthalmic surgical system;
  evaluating the signal with the geometric size of the pupil which was captured at the first time during the surgical procedure on the eye by a comparison with a geometric reference size of the pupil;
  outputting an output signal, which contains information in respect of the geometric size of the pupil and/or information in respect of the comparison of the captured geometric size of the pupil with the reference size of the pupil, by means of an output module of the ophthalmic surgical system, in particular to a control unit of the ophthalmic surgical system and/or on an output unit, in particular of the ophthalmic surgical system, for a user.

In particular, the computer program product comprises commands which, when the program is executed by a computer, prompt the latter to carry out a method for controlling a fluidic apparatus of an ophthalmic surgical system including the following further steps:
  setting an operating state, in particular at least one pressure and/or a volumetric flow, in particular in an irrigation line of an irrigation apparatus and/or in an aspiration line of an aspiration apparatus, of a fluid of the fluidic apparatus on the basis of the output signal using a control unit of the ophthalmic surgical system during the surgical procedure, in particular phacoemulsification, on the eye to be treated.

One aspect of the invention relates to a computer program product comprising commands which, when the program is executed by a computer, prompt the latter to carry out a method for controlling a fluidic apparatus of an ophthalmic surgical system including the following further steps:
  setting first fluidic parameters of a fluidic apparatus of the system and supplying fluid to and/or removing fluid from an eye on the basis of the first fluidic parameters set at a first preparation time;
  providing a geometric size of a pupil of an eye to be treated, during and/or after the supply of the fluid and/or removal of the fluid, on the basis of the first fluidic parameters, to a receiver module of the ophthalmic surgical system;
  providing a geometric size of the pupil of the eye to be treated, which occurred at least at one second preparation time, following the first preparation time, or shortly thereafter, prior to which an artificial occlusion was produced in the eye and/or prior to which an artificial break of an occlusion was produced in the eye, to the receiver module;
  evaluating the geometric sizes of the pupil that occurred at the different preparation times by means of an evaluation unit of the ophthalmic surgical system.

In particular, the computer program product comprises commands which, when the program is executed by a computer, prompt the latter to carry out a method for controlling a fluidic apparatus of an ophthalmic surgical system including the following further steps:
  setting an operating state, in particular at least one pressure and/or a volumetric flow, in particular in an irrigation line of an irrigation apparatus and/or in an aspiration line of an aspiration apparatus, of a fluid of the fluidic apparatus on the basis of the evaluated geometric sizes of the pupil of the fluidic apparatus, using a control unit of the ophthalmic surgical system on the basis of the evaluated geometric sizes of the pupil during a surgical procedure, in particular phacoemulsification, on the eye to be treated and/or
  providing the value of the pressure and/or the value of the volumetric flow on an output unit, in particular of the ophthalmic surgical system, for a user.

In particular, the computer program product also comprises commands which, when the program is executed by a computer, prompt the latter to carry out a method for controlling a fluidic apparatus of an ophthalmic surgical system including the following further steps:
  capturing the geometric size of the pupil of the eye to be treated, during and/or after the supply and/or removal of the fluid at the first preparation time and at the at least second preparation time using an optical capturing apparatus of the ophthalmic surgical system;
  supplying signals with the captured geometric sizes of the pupil to the receiver module.

One aspect also relates to a computer-readable storage medium with a computer program product as per the aforementioned aspect. This can also be a computer-readable data medium, on which the computer program product as per the aforementioned aspect is stored.

One aspect of the invention relates to a method for determining fluidic parameter settings of a fluidic apparatus of an ophthalmic surgical system during a preparation phase before a surgical procedure on an eye to be treated, in which the following steps are carried out:
- receiving a signal with a geometric size of a pupil of the eye to be treated, during and/or after the supply of the fluid and/or removal of fluid, on the basis of first fluidic parameters set at a first preparation time during the preparation phase, by a receiver module of the ophthalmic surgical system;
- receiving a further signal with a geometric size of the pupil of the eye to be treated, which occurred at least at one second preparation time during the preparation phase, following the first preparation time, or shortly thereafter, prior to which an artificial occlusion was produced in the eye and/or prior to which an artificial break of an occlusion was produced in the eye, by the receiver module;
- evaluating the geometric sizes of the pupil that occurred at the different preparation times by means of an evaluation unit of the ophthalmic surgical system;
- in particular, determining an operating state, in particular at least one pressure and/or a volumetric flow, in particular in an irrigation line of an irrigation apparatus and/or in an aspiration line of an aspiration apparatus of a fluid of the fluidic apparatus, of the fluidic apparatus, using the evaluation unit of the ophthalmic surgical system on the basis of the evaluated geometric sizes of the pupil for a subsequent surgical procedure, in particular phacoemulsification, on the eye to be treated and/or
- in particular, providing the value of the pressure and/or the value of the volumetric flow on an output unit, in particular of the ophthalmic surgical system, for a user.

In particular, the method also includes the following steps:
- receiving a plurality of further signals, each with a geometric size of the pupil of the eye to be treated, which occurred at least at preparation times during the preparation phase, following the first preparation time, or shortly thereafter, prior to which an artificial occlusion was produced in the eye and/or prior to which an artificial break of an occlusion was produced in the eye, by the receiver module;
- evaluating this plurality of signals in terms of which has the smallest geometric size of the pupil, by the receiver module and/or the evaluation unit;
- determining this smallest geometric size as the size captured at the second preparation time, by the communications module and/or the evaluation unit;
- comparing this smallest geometric size of the pupil to the geometric size of the pupil at the first preparation time, in particular forming a ratio between the geometric size at the first preparation time and the smallest geometric size as respective actual ratios, by the evaluation unit;
- in particular, comparing the actual ratio formed to a specified intended ratio;
- in particular, assessing the fluidic parameter values set at the first preparation time on the basis of the comparison in view of a setting suitable for a surgical procedure on the eye, in particular determining at least one reference fluidic parameter setting.

A further aspect of the invention relates to the use of a control apparatus as per one of the aforementioned aspects or an advantageous embodiment thereof, for controlling a fluidic apparatus of an ophthalmic surgical system, in particular for controlling fluidic parameters of a fluid of the fluidic apparatus.

A further aspect relates to a control apparatus as per one of the aforementioned aspects or an advantageous embodiment thereof, to be used when controlling a fluidic apparatus of an ophthalmic surgical system, in particular when controlling fluidic parameters of a fluid of the fluidic apparatus during phacoemulsification.

The concrete values indicated in the documents for parameters and indications concerning ratios of parameters or parameter values for the definition of embodiments of the eye lens should be considered to be concomitantly encompassed by the scope of the invention even in the context of deviations, for example on account of measurement errors, system faults, DIN tolerances, et cetera, which means that explanations relating to substantially corresponding values and indications should also be understood thereby.

BRIEF DESCRIPTION OF THE DRAWINGS

The invention will now be described with reference to the drawings wherein.

DESCRIPTION OF THE PREFERRED EMBODIMENTS OF THE INVENTION

In the figures, identical or functionally equivalent elements are provided with the same reference signs.

Figure 1:
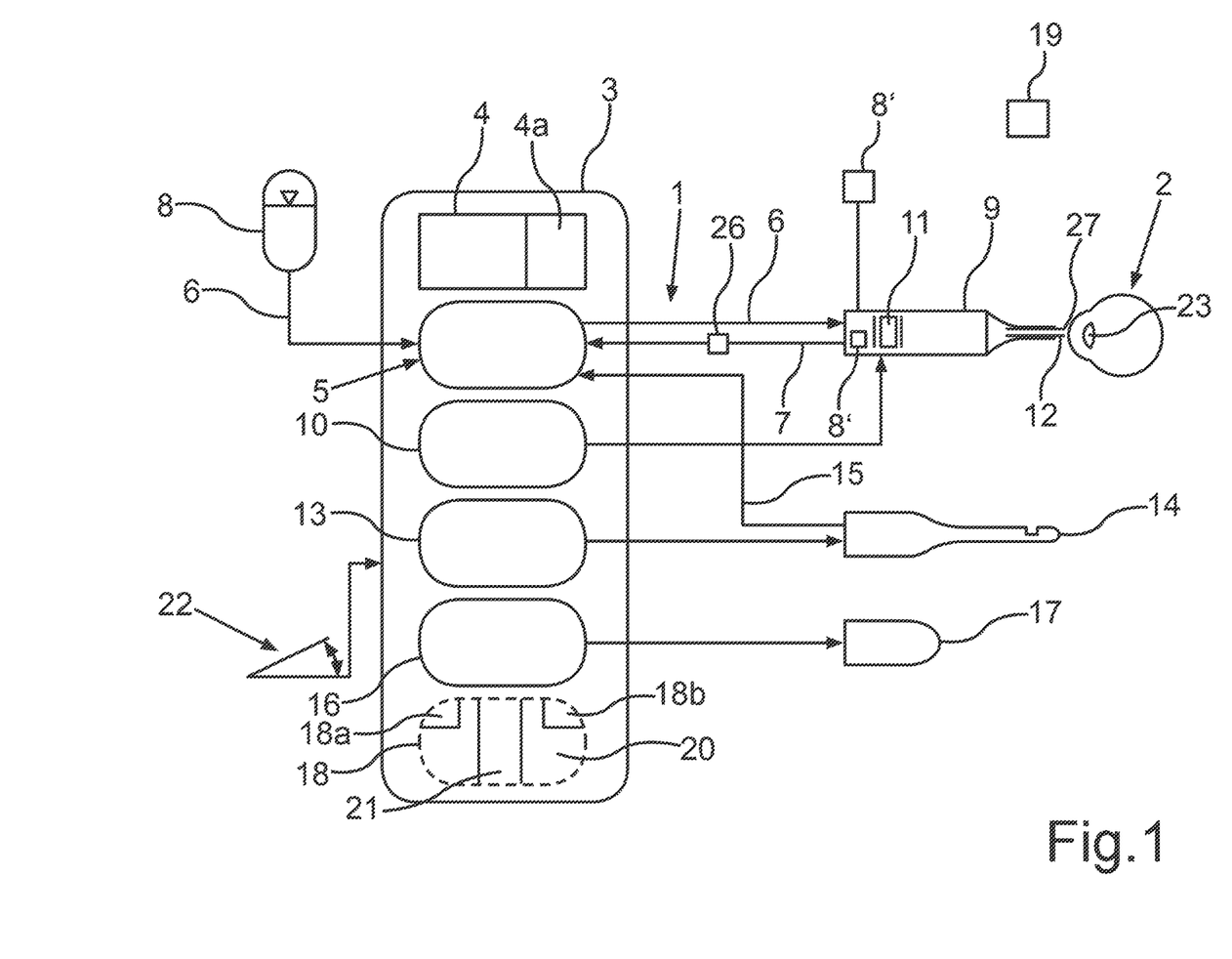
FIG. 1 shows a schematic illustration of an embodiment of an ophthalmic surgical system showing an embodiment of a control apparatus.

FIG. 1 shows a schematic of an ophthalmic microsurgical system or an ophthalmic surgical system 1 for phaco-surgery on an eye 2. The illustration according to FIG. 1 shows a few of the components of the system 1 in symbolic fashion for a simplified explanation of the basic general functionality of the system 1.

The system 1 comprises a device unit 3, which can be, for example, a trolley or the like. Preferably, an operating unit 4 is arranged in or on the device unit 3. By way of example, this operating unit 4 may comprise a user interface, an input unit such as a keyboard or the like and a display unit, in particular as an output unit 4a, such as a monitor or display. Furthermore, a fluidic apparatus 5 that comprises a pump and a control unit for controlling the pump and connected components, in particular, is preferably arranged in the device unit 3. The fluidic apparatus 5 comprises an irrigation apparatus 6 with an irrigation branch or an irrigation line and an aspiration apparatus 7 with an aspiration branch or an aspiration line. The irrigation apparatus 6 comprises a container 8 for rinsing liquid, for example a BSS solution, which is a fluid for irrigation and which is guided to a phaco-handpiece. The phaco-handpiece is an ophthalmic surgical handpiece 9. In particular, it is a constituent part of the ophthalmic surgical system 1. The aspiration apparatus 7 is likewise connected to the ophthalmic surgical handpiece 9. Moreover, the device unit 3 comprises an ultrasonic unit 10 in particular, the latter being embodied to excite an oscillation of piezoelectric elements 11 in the ophthalmic surgical handpiece 9, by means of which a hollow needle 12 of the ophthalmic surgical handpiece 9 is excited to oscillate. Further, the device unit 3 comprises a control unit 13, in particular. The control unit 13 can also be embodied to control a vitrectomy handpiece 14, which, in particular, may be a constituent part of the ophthalmic surgical system 1. Preferably, the vitrectomy handpiece 14 is also connected to the fluidic apparatus 5, in particular by a further aspiration line 15. Moreover, provision can be made for a further control unit 16, the latter controlling a preferably available further surgical instrument 17, for example for diathermy. Moreover, the system 1 and, in particular, the device unit 3 could comprise further modules. This also comprises further internal units, and also peripheral devices.

Moreover, the ophthalmic surgical system 1 preferably comprises a foot control panel 22, which is connected to the device unit 3, more particularly to communication devices and control units of the device unit 3.

Moreover, FIG. 1 schematically shows a natural lens 23 in the eye 2. This lens 23 can be removed by the ophthalmic surgical system 1, in particular by phacoemulsification.

In an alternative embodiment, provision can be made for the ophthalmic surgical system 1 to comprise a tank 8' (FIG. 1) that is separate from the container 8. In such an embodiment, the cooling fluid, which is provided to cool the incision, is provided separately from the irrigation apparatus 6 and separately from the container 8. The tank 8' can be arranged separately from the handpiece 9 and, for example, can be connected to the handpiece 9 via a line, such as a tube connection.

In a further embodiment, provision can be made for the separate tank 8' to be arranged in the handpiece 9. It can be arranged in the handpiece 9 in a non-destructively non-detachable or non-destructively detachable fashion. Provision could also be made for a first separate tank 8' to be arranged in the handpiece 9 and for a further separate tank 8' to be arranged outside of the handpiece 9. This further tank 8' outside of the handpiece 9 can be connected in fluid-conducting fashion to the tank 8' arranged in the handpiece 9.

In particular, this ophthalmic surgical system 1 comprises a control apparatus 18. In particular, this control apparatus 18 comprises at least one receiver module 18a.

The ophthalmic surgical system 1 preferably comprises at least one optical capturing apparatus 19. In particular, at least one geometric size of a pupil of the eye 2 to be treated can be captured with this optical capturing apparatus 19. This can be carried out, in particular, at least at one first time during a surgical procedure on the eye, at which fluid is or has been supplied to and/or is or has been removed from the eye 2 to be treated on the basis of set values of fluidic parameters of the fluidic apparatus 5. Likewise, the geometric size of the pupil can be also captured by the optical capturing apparatus 19 during a preparation phase before the surgical procedure. This can be carried out, in particular, at least at one first preparation time during the preparation phase. During the preparation phase, the hollow needle 12 has been injected into the eye 2 but is arranged at such a distance from the capsular bag and the natural lens 23 in the eye 2 that there is no impairment by the hollow needle 12 in the case of a movement of the capsular bag with the lens 23, in contrast to the actual surgical procedure. In particular, there has not yet been any artificial production of an occlusion or a breakthrough of the occlusion in the eye 2 at this first time, which is during a preparation phase prior to an actual phacoemulsification. Thus, an influence state on the eye 2, in particular, is also produced at this first preparation time. This influence state differs from a normal state of the eye 2, in which no surgical instrument has been inserted into the eye 2 and no other surgical examination influence is exerted on the eye 2.

The optical capturing apparatus 19 is further embodied to allow the capture of at least one geometric size of the pupil of the eye 2 to be treated at least at one second preparation time during the preparation phase, prior to which an artificial occlusion was produced in the eye 2 and/or an artificial breakthrough of the occlusion was produced in the eye 2. This is generated artificially and in time-defined fashion, in particular immediately before the second time of the breakthrough of the occlusion, that is, in particular less than 200 ms therebefore.

In one embodiment, the control apparatus 18 includes:
a receiver module 18a which allows a signal to be received, the latter containing at least one geometric size of a pupil 25 (for example, FIG. 2A) of an eye 2 to be treated at least at one first time during a surgical procedure on the eye 2, at which fluid is or has been supplied to and/or removed from the eye 2 to be treated on the basis of set values of fluidic parameters of a fluidic apparatus 5 of the ophthalmic surgical system 1;

an evaluation unit 20 which allows the signal with the geometric size of the pupil 25 which was captured at the first time during the surgical procedure on the eye 2 to be compared to a geometric reference size of the pupil 25;

an output module 18b which allows the output of an output signal of the evaluation unit 20, which contains information in respect of the geometric size of the pupil 25 and/or information in respect of the comparison of the captured geometric size of the pupil 25 with the reference size of the pupil 25, in particular allows the output thereof to a control unit 21 of the ophthalmic surgical system 1 and/or allows the output thereof on an output unit 4a, in particular of the ophthalmic surgical system 1, for a user.

In particular, the control apparatus 18 comprises a control unit 21 by means of which, during the surgical procedure, in particular phacoemulsification, of the eye 2 to be treated, at least one pressure and/or a volumetric flow, in particular in an irrigation line of an irrigation apparatus 6 and/or in an aspiration line of an aspiration apparatus 7, of a fluid of the fluidic apparatus 5 is adjustable on the basis of the output signal of the output module 18b and/or the value of the pressure and/or the value of the volumetric flow is providable, more particularly provided, on the output unit 4a, in particular of the ophthalmic surgical system 1, for a user.

In this embodiment, the control apparatus 18 is arranged outside of the optical capturing apparatus 19.

In a further embodiment, provision can be made for the receiver module 18a, the evaluation unit 20 and the output module 18b to be constituent parts of the optical capturing apparatus 19. In this further embodiment, these components are integral constituent parts of the optical capturing apparatus 19. In a further embodiment, the control unit 21, in particular, is arranged outside of the optical capturing apparatus 19 and is not a constituent part of the optical capturing apparatus 19.

In a yet further embodiment, provision can be made for the optical capturing apparatus 19 to only comprise the receiver module 18a of the control apparatus 18.

In particular, provision can be made for at least two such different fluidic parameter settings to be set as basic settings during a preparation phase or test phase before the phacoemulsification to be actually carried out on the eye 2 to be treated. This is respectively followed in time by, in particular, an artificially produced break of an occlusion during this preparation phase and the geometric size of the pupil is also optically captured in each case here, particularly shortly after this event. In particular, the geometric size of the pupil can be captured, in particular in individual images or as a video, by the optical capturing apparatus 19 over the entire time duration during this preparation phase, from the break of the occlusion up to the standstill of the movement of the lens 23 and of the capsular bag in the eye 2.

In particular, the fluidic parameters relate to a pressure and/or a volumetric flow of the fluid in the aspiration line of the aspiration apparatus 7. In addition or as an alternative thereto, the fluidic parameters can relate to a pressure and/or a volumetric flow of the fluid in the irrigation line 6. In respect of the fluidic parameters of the fluid in the irrigation line, it is also possible to take account of the height of the container 8 in relation to a reference level, in particular the floor, at which the ophthalmic surgical system 1 has been set up. Taking account of this height, it is possible to determine a pressure of the fluid in the irrigation line.

In particular, this fluid is supplied into the eye 2 during this preparation phase, and so it is possible to assess during this preparation phase the reaction of this eye 2 to be treated on the basis of this individual fluid supply, as is then defined by the fluidic parameter settings.

The optical capturing apparatus 19 is preferably a surgical microscope. Therefore, it is not necessary to use an optically complicated and expensive OCT system. The surgical microscope can comprise the output module 18b. The optical capturing apparatus 19 can also comprise at least one camera.

This also allows decision information to be providable for a selection of a physical operation component during the subsequent phacoemulsification, which also includes the implantation of an intraocular lens into the eye 2, of the eye 2 to be treated on the basis of these evaluated geometric sizes of the pupil 25.

In particular, the control apparatus 18 also allows different fluidic parameter settings to be set during the specified preparation phase and allows a potential occlusion and/or a potential break of an occlusion to be simulated very realistically or to be artificially produced. This then allows the determination and prediction of very precise conclusions in respect of the reaction of the eye 2 during the subsequent actual phacoemulsification, during which an actual occlusion and an actual break of such an occlusion may occur. As a result of the aforementioned advantageous embodiment, in which these evaluated geometric sizes obtained during the preparation phase are used as a basis for setting the operating state of the fluidic apparatus 5 during the subsequent phacoemulsification, it is possible to very exactly set the operating state in order to identify an actual occlusion during the phacoemulsification and/or an actual break in best possible and timely fashion and in order to be able to react very precisely thereto. In particular, an adapted fluid supply and an adapted fluid removal from the eye 2 are carried out as a result of this operating state then set in the case of such an occlusion. The same then also applies to a break of an occlusion during the phacoemulsification. Such a state can also be implemented by the control unit 21 by setting the very specific operating state of the fluidic apparatus 5 to the effect that the eye 2 remains in a virtually stable state, even in the case of such a break. This means that the movement of the capsular bag and of the lens is reduced, in particular that, following a break of the occlusion, an overshoot beyond a relative reference position toward the cornea can be at least reduced. The disadvantages set forth at the outset, which may occur as a result of an occlusion and/or break of such an occlusion during phacoemulsification and which can accordingly impair the eye 2, can be at least significantly reduced by this procedure.

Provision can also be made for the control unit 13 and/or the control unit 16 to be constituent parts of the control apparatus 18.

Provision can also be made for one of the control units 13 and/or 16 to be the control unit 21.

For the geometric size of the pupil, provision can also be made for an area or a change in area of this pupil to be taken into account and/or for a diameter or a change in diameter of the pupil to be taken into account. In particular, such an area is considered in a plane, in particular a projection plane, in the case of a plan view of the eye 2 to be treated.

In the case of a break of an occlusion, there is a fast and significant drop of pressure in the ocular chamber on account of the volumetric flows in the irrigation line and in the aspiration line, which change over a very short period of time, and there subsequently is a reduction in the volume of the anterior chamber of the eye. The pressure drop can lead to the cornea sinking in. Contact between the inner side of the cornea and surgical instruments introduced into the eye may damage the internal terminating corneal tissue, the endothelium. A significantly damaged endothelium may lead to necrosis of the cornea. A further disadvantage that may occur as a result of this instability in the eye on account of the different inflows and outflows is an aspiration of the back capsular bag wall. The break of the occlusion can lead to the aspiration of the back capsular bag wall in the case of eyes where the lens has been removed. In the process, the thin skin of the capsular bag can be permanently injured and this can make the subsequent insertion of the intraocular lens significantly more difficult. The task is to avoid these impairments and this is facilitated, in particular, using the aforementioned control apparatus 18, and so an anterior chamber of the eye 2 that is as stable as possible during actual phacoemulsification is facilitated. Consequently, such an instability in the eye 2 is, in particular, a change in the volume, in particular a change in the form, of the anterior chamber of the eye.

In addition to determining the geometric size of a pupil of the eye 2 to be treated, it is also possible to capture and assess at least one eye part of the eye 2 that differs from the pupil. In particular, this can also be implemented during the preparation phase in order to also carry out appropriate analyses in this case, as have already been explained above in respect of the geometric size of the pupil. In particular, it is also possible, to this end, to capture a geometric size of the eye part at least at two different preparation times. In particular, this can also be implemented using the optical capturing apparatus 19. By way of example, the limbal ring of the eye 2 to be treated and/or the cornea of the eye 2 to be treated and/or the sclera of the eye 2 to be treated and/or the capsular bag of the eye 2 to be treated can be specified as such a different eye part. In particular, it is also possible to capture and assess a geometric size in the case of the limbal ring, in particular the area and/or the diameter. Using this, it is also possible to draw conclusions about an occlusion and/or a break of the occlusion on the basis of changes in size in the case of these different fluidic parameter settings. The limbal ring describes the boundary between the iris, the cornea and the sclera.

Observing the cornea advantageously allows a formation of folds to be captured optically. These folds form on the cornea in the case of a transition from a stable chamber with a convex cornea to a collapsed chamber. Consequently, the occurrence of such folds is considered to be an indication of an unstable chamber. An increase in the corneal radius is expected before the occurrence of such folds in the case of a drop in pressure in the eye, in particular in the anterior chamber of the eye.

Additionally, the structure or the pattern of the iris can also be captured during these different fluidic parameter settings and can be used for the assessment as to whether an occlusion is imminent or has taken place and/or whether a break of an occlusion is imminent or has taken place.

In particular, a possible tilt of the eye 2 to be treated, which may affect the analysis, is also taken into account. This can be carried out using known image evaluation methods.

In view of setting the operating state of the fluidic apparatus 5 by the control unit 21, the latter can be implemented during the surgical procedure, in particular the phacoemulsification, to the effect of there being a message to the surgeon that there is a need for action and/or, optionally, which action is needed to stabilize the anterior chamber of the eye. Provision can also be made for the control unit 21 to independently and automatically operate the fluidic apparatus 5 so as to be able to counteract a destabilizing event. This also is the setting of such a specific operating state. These courses of action can be both for the short term and for the long term. This allows immediate events to be counteracted in the short term and for a restricted amount of time.

At least the first values of the fluidic parameters and/or the captured geometric sizes and/or the evaluated geometric sizes can be displayed on the output unit 4a of the operating unit 4.

Figure 2A:
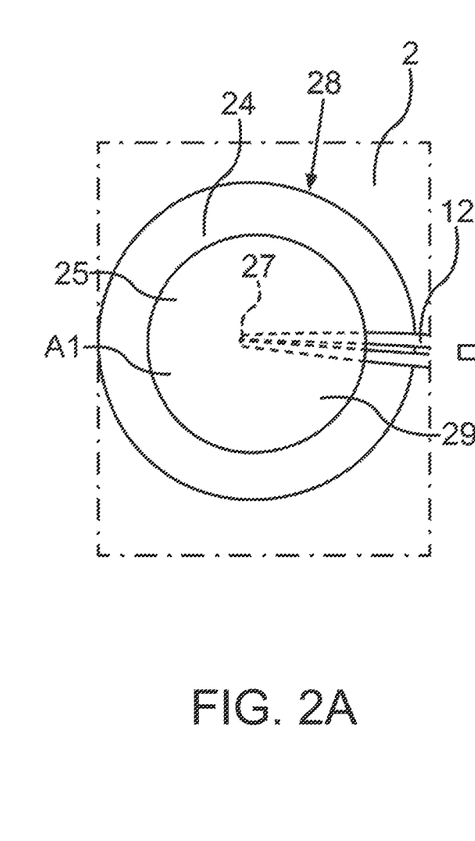
FIG. 2A shows a plan view of a portion of an eye to be treated, in which the eye to be treated is shown in an influence state and a geometric size of the pupil of this eye is shown as a reference.
Figures 2B, 2C:
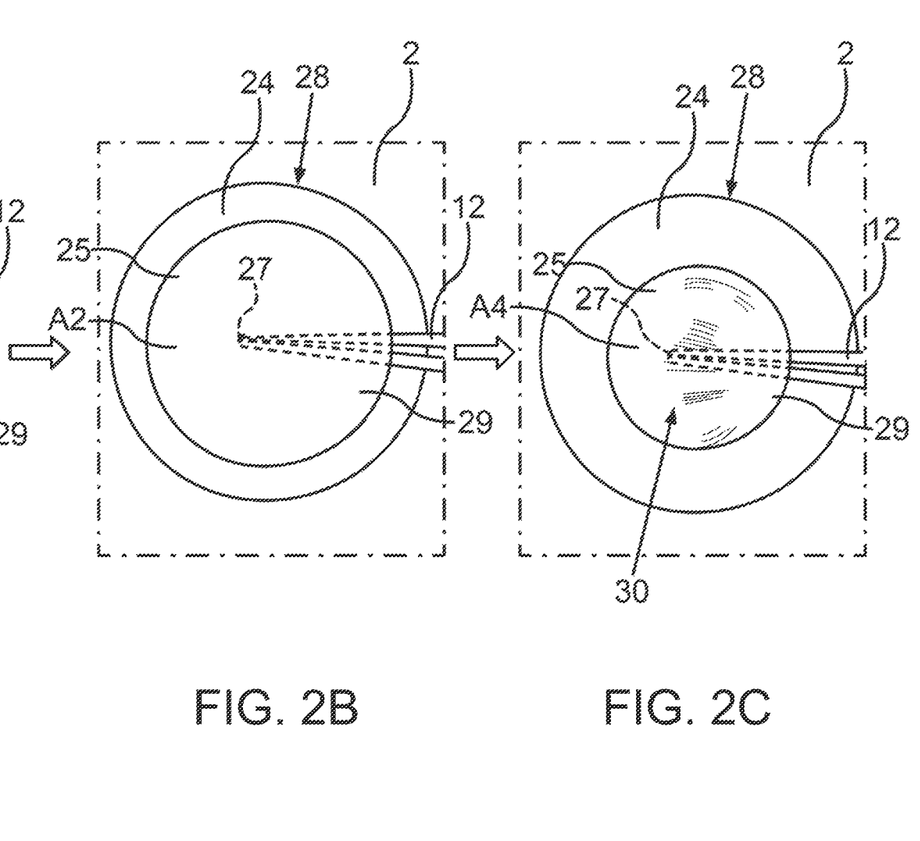
FIG. 2B shows the portion of the eye to be treated as per FIG. 2A in a state of an artificially produced occlusion or in an artificially produced occlusion-like state during a preparation phase before a surgical procedure, wherein the geometric size of the pupil has increased in relation to the reference in FIG. 2A in this artificially produced state.
FIG. 2C shows the portion of the eye to be treated, as per FIGS. 2A and 2B, in a state of an artificially produced breakthrough of the occlusion or in an artificially produced occlusion breaking-like state, wherein the geometric size of the pupil has decreased in relation to FIG. 2A and FIG. 2B.

FIG. 2A shows a plan view of a portion of the eye 2 to be treated, with a pupil 25 being surrounded by an iris 24. Shown here is a state in which the eye 2 to be treated is in a stable state during this preparation phase prior to phacoemulsification; this state is denoted an influence state, as already mentioned above. Here, an area A1 of the pupil 25 is shown as a reference. The absolute value of the area A1 is equated to an opening size of the pupil 25 of 100 percent. Proceeding from this state at a first preparation time, fluidic states are set during this preparation phase. In the process, an occlusion-like state is also set artificially. By way of example, the aspiration line of the aspiration apparatus 7 can be bent to this end or the volumetric flow flowing therein can be reduced in any other way such that the throughflow is significantly reduced or prevented. This is shown in FIG. 2B. However, preferably, a magnetic valve 26 (FIG. 1) could also be arranged in the aspiration line of the aspiration apparatus 7, which magnetic valve can be opened and closed accordingly.

What was found in this set state, which is shown in FIG. 2B, is that there has been a change in the geometric size of the pupil 25; in particular, the latter has increased to the area A2. By way of example, an increase by up to 10 percent in comparison with the area A1 may occur here. This, too, is optically captured by the optical capturing apparatus 19. As may be identified in FIGS. 2A and 2B, the tip 27 of the hollow needle 12, in particular, has been introduced during this preparation phase into the eye 2 to be treated so that fluid can be supplied by the irrigation line of the irrigation apparatus 6 and can be aspirated from the eye 2 to be treated by the aspiration line of the aspiration apparatus 7. Proceeding from the state shown in FIG. 2B, the break of the occlusion can then be produced artificially during the preparation phase. By way of example, this can be simulated or artificially produced by ending the bend in the aspiration line or, if a magnetic valve 26 is preferably present, by opening the magnetic valve 26. In particular, in this context, it is consequently also possible to break up an occlusion simulated as per FIG. 2B and, as per the illustration in FIG. 2C, bring about such a break of an occlusion, which was simulated or produced in an artificially defined fashion, as an occlusion breaking-like state.

As may be identified in the illustration of FIG. 2C, there once again is a characteristic change in the geometric size of the pupil 25 in this context. Specifically, there is a reduction to the area A4. This reduction occurs both in relation to the reference, specifically the area A1 as per FIG. 2A, and in relation to the increased area A2 as per FIG. 2B. In particular, there are reductions here of up to 10 percent, in particular of up to 8 percent, in comparison with the reference in FIG. 2A.

Provision can be made for a respective influence state to be produced at a plurality of different preparation times during the preparation phase, the influence states being different as their values of the fluidic parameters are set in defined different fashion. Hence, an even more precise statement can be made during the preparation phase in respect of the reaction of the eye 2 to be treated in the case of specific states, in particular in the case of a potential occlusion and/or a potential break of such an occlusion.

In addition to observing the area of the pupil 25 in the case of these different fluidic parameter settings during the preparation phase for phacoemulsification, further characteristic eye parts can be observed in respect of their geometric size. In particular, this relates to a limbal ring 28. Here, too, the corresponding change in area can also be observed and evaluated. In particular, this can be implemented in accordance with what was explained above and will be explained below in relation to the pupil. In addition or as an alternative thereto, it is also possible to capture and assess a sclera, which is not shown in FIG. 2A to 2C. It is also possible to observe a cornea 29 of the eye 2 to be treated. In particular, it is possible to identify in this context that folds 30 occur in the cornea 29 in the case of a state as per FIG. 2C and consequently in the case of such a simulated break of the occlusion. The folds can likewise be captured by the optical capturing apparatus 19.

Figure 3A:
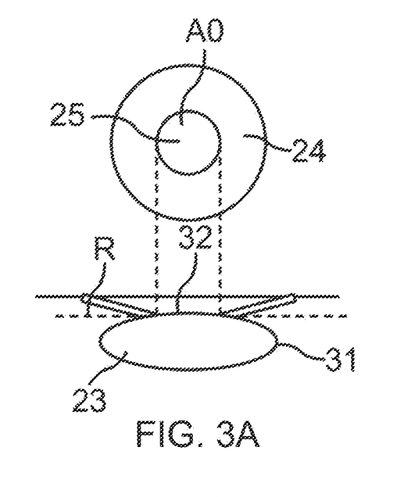
FIG. 3A shows a position of a capsular bag with a lens in an eye in a normal state, in which no surgical instrument has been inserted into the eye.

Below, FIG. 3A to FIG. 3F are used to explain the processes occurring in the eye 2 to be treated when these different stability states occur in the eye 2 on account of the corresponding fluidic states. FIG. 3A shows the aforementioned normal state. The capsular bag 31 with the lens 23 is arranged in a specific relative position. In a plan view of the eye 2, this results in a visible area A0 of the pupil 25.

Figure 3B:
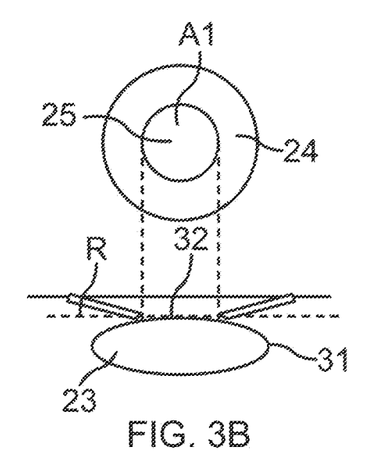
FIG. 3B shows a schematic of a position of the capsular bag with the lens in an influence state, in which a surgical instrument has been inserted into the eye and/or fluidic parameters have been preset.

FIG. 3B shows a schematic illustration in which the eye 2 is in an aforementioned influence state. A hollow needle 12 is pierced into the eye 2 and fluid is supplied by the irrigation line and/or removed by the aspiration line. As a result, this also sets first values of fluidic parameters at a first time. In this influence state, the pupil 25 has a visible area A1 in the plan view. This area A1 is slightly larger than the area A0. This area A1 can be a reference size of the pupil 25. It can be predetermined as a reference size.

What was found here is that, in the state as per FIG. 3B and in the lower illustration in that case which shows a simplified sectional view, a lens 23 in a capsular bag 31 is arranged in a relative reference position or reference position R when the interior of the eye 2 to be treated is stable. In this context, the reference position R is defined, for example, in relation to a front side 32, in particular a maximum of the convexly curved front side 32, which faces the cornea 29. In FIG. 3B, first values of fluidic parameters, which cause this stable relative position of the lens 23, have been set.

Figure 3C:
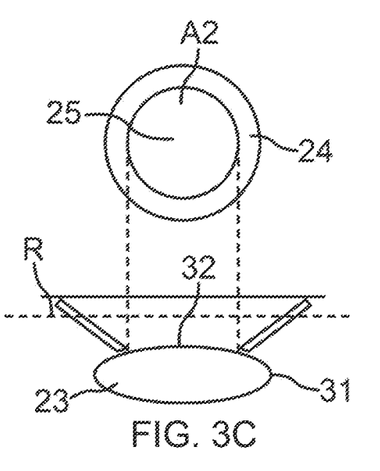
FIG. 3C shows a schematic of a position of the capsular bag with the lens in a state in which an occlusion has been produced in an aspiration line.

If the pressure in the interior of the eye 2 is now increased and consequently more fluid is supplied than aspirated, as already explained in relation to FIG. 2B, it is possible to identify that the lens 23 has moved out of its reference position R as per FIG. 3B; specifically, it is moved further away from the cornea 29. This is shown in the lower illustration of FIG. 3C. Accompanying this, it was observed that the pupil 25 increases to the area A2 in comparison with the area A1, as shown in FIG. 3C in the schematic plan view of the upper illustration there. In particular, this is caused by an occlusion-like state, which causes this reaction in the eye 2. Thus, FIG. 3C shows the position of the capsular bag 31 and of the lens 23 in the case of an occlusion.

Figure 3D:
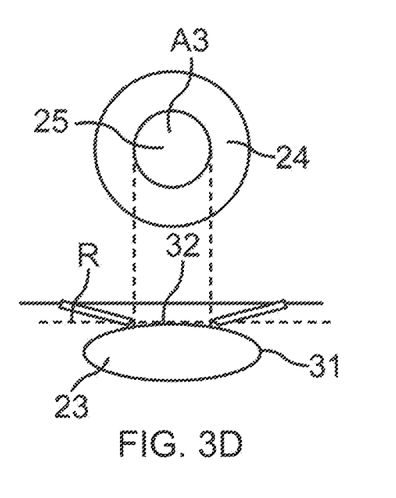
FIG. 3D shows a schematic of a position of the capsular bag with the lens in a state in which a breakthrough of an occlusion in an aspiration line has been produced and there is a setting of at least one fluidic parameter in the case of which the smallest geometric size of the pupil, which occurred during the movement of the lens and the capsular bag, is the same size or substantially the same size as in the influence state as per FIG. 3B.
Figure 3E:
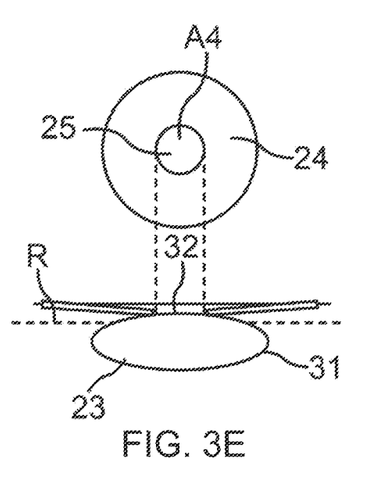
FIG. 3E shows a schematic of a position of the capsular bag with the lens in a state in which a breakthrough of an occlusion in the aspiration line has been produced and there is a setting of at least one fluidic parameter in the case of which the smallest geometric size of the pupil, which occurred during the movement of the lens and the capsular bag, is significantly smaller than in the influence state as per FIG. 3B.

If then, proceeding from the state in FIG. 3C, a break of such an occlusion is produced, in particular if an occlusion breaking-like state is caused, it was observed that the lens 23 can carry out a movement toward the cornea 29; see FIG. 3D and FIG. 3E. This is effected by way of moving beyond the reference position R. Consequently, there is, as it were, a certain amount of overshoot beyond the reference position R, shown in FIG. 3B, to the cornea 29, as shown in FIG. 3E. In this context, it was also possible to determine that the area A4 of the pupil 25 is set. The area A4 is smaller than both the area A2 and the area A1. The position of the lens 23 is shown in the lower illustration of FIG. 3E; the area A4 is shown in the upper plan view illustration of FIG. 3E.

Figure 3F:
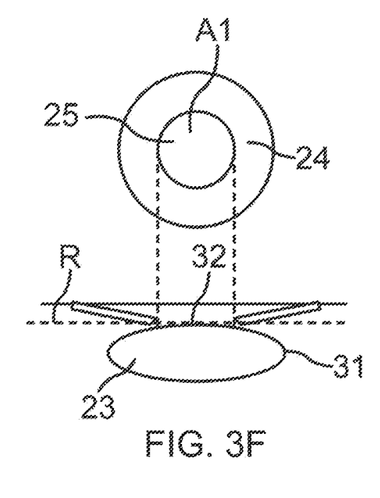
FIG. 3F shows a schematic of a position of the capsular bag with the lens in a state as per FIG. 3B.

Proceeding from this position in FIG. 3E, the lens 23 then moves back into the initial relative position, as was illustrated in FIG. 3B and as is shown again in FIG. 3F. This is once again accompanied by a change in the pupil 25, from the area A4 to the area A1, as shown in FIG. 3F. These processes in the eye 2 relate to the lens 23 and the capsular bag 31. Consequently, they relate to the change in size of the pupil 25, in particular the change in area of the pupil 25. This accompanies the change in pressure in the eye 2. Hence, as already presented above, very precise statements about the reaction of the eye 2 to be treated can be made in the case of the different fluidic parameter settings by way of using the relatively simple optical capture of this area of the pupil 25 in these different fluidic parameter settings. Particularly if these fluidic parameter settings are occlusion-like states and/or occlusion breaking-like states, very precise conclusions can consequently be drawn during the preparation phase as to which actual fluidic parameter settings are required during the phacoemulsification in order to be able to maintain a more or less stable state in the eye 2, even in the case of an occlusion during the phacoemulsification or a break of an occlusion during the phacoemulsification. Then, these settings are reference fluidic parameter settings.

In order to avoid the position of the lens 23 as per FIG. 3E, and hence in order to avoid or at least significantly reduce the overshoot, the areas of the pupil 25 are captured during the preparation phase following the artificially produced break of the occlusion, at least at a preparation time, in particular at a plurality of preparation times, in particular continuously, by means of the optical capturing apparatus 19. Thus, for example, FIG. 3D shows an illustration that has occurred after the artificial break of the occlusion. An area A3 of the pupil 25 has been captured by the capturing apparatus 19. In particular, this is the smallest area that occurred during the travel of the capsular bag 31 and the lens 23 following an artificially produced break of the occlusion, from the relative position in FIG. 3C, which also counts as an example of an artificially produced occlusion, up to the standstill of the capsular bag 31 and the lens 23. The changes in area of the pupil 25 accompanying this movement are captured. This smallest area A3 is then considered to be the area captured at a second preparation time.

If this smallest area A3 is smaller than the area A1, the capsular bag 31 and the lens 23 have overshot the relative reference position R toward the cornea 29. By forming a ratio from the actual ratios of the geometric sizes of the pupil 25, in particular the areas A1 and A3 at the two preparation times, it is possible to identify that these associated set first values of the fluidic parameters are not suitable, for example, to sufficiently prevent the overshoot in this specific eye 2 during the actual surgical procedure. In particular, this ratio of the areas A1/A3 is compared to a specified intended ratio. This intended ratio preferably equals 1.

Since the ratio A1/A3 is (significantly) greater than 1 in this case, this fluidic parameter setting is unsuitable. It therefore does not represent a reference fluidic parameter setting.

If this smallest area A3 is greater than the area A1, then the capsular bag 31 and the lens 23 no longer reach the relative reference position R with this specific fluidic parameter setting. Then, the ratio A1/A3 is (significantly) less than 1 in this case. These could be reference fluidic parameter settings.

However, if this smallest area A3 has the same size as the area A1, or at least substantially the same size, as shown in FIG. 3D, for example, it is possible to identify that the lens 23 and the capsular bag 31 have reached the relative reference position R without overshooting beyond the relative reference position R. Then, the ratio A1/A3 equals 1 or substantially equals 1. Hence, a fluidic parameter setting has been identified, which is advantageous for the specific eye 2 in a subsequent surgical procedure for the purposes of avoiding an overshoot. They therefore represent a reference fluidic parameter setting.

The geometric size of at least the pupil 25 can be captured, in particular continuously, by the optical capturing apparatus 19 during the subsequent surgical procedure. Thus, the evaluation unit can compare this captured geometric size of at least the pupil 25 with the predetermined geometric reference size, in particular using the evaluation unit 20. It is possible to determine, in particular continuously determine, a deviation or a change in the deviation of the geometric size of at least the pupil 25 from the geometric reference size of at least the pupil 25. Depending thereon, it is then possible to identify at least one state during the surgical procedure, in the case of which a real break of a real occlusion is imminent. It is then possible to react thereto by virtue of setting a reference fluidic parameter setting. Consequently, what can also be achieved is that an area A4, as explained above, no longer occurs during the surgical procedure. This is successful since is it possible to avoid an overshoot of the capsular bag 31 beyond the relative reference position R toward the cornea 29. In particular, this also renders it possible to avoid the tip 27 injuring the back capsular bag wall.

Figure 4:
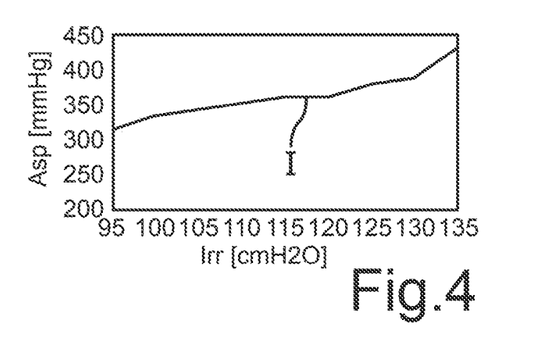
FIG. 4 shows a diagram, in which two different fluidic parameters of a fluidic apparatus of the ophthalmic surgical system as per FIG. 1 are plotted and a characteristic line is illustrated, the latter indicating the specific fluidic parameter value pairs at which the geometric size of the pupil of the eye to be treated in the state as per FIG. 3D equals the geometric size of the pupil in the influence state as per FIG. 3B; and, FIG. 5 shows a diagram as per FIG. 4, showing the characteristic line for a different eye to that of FIG. 4.

FIG. 4 shows, in a simplified example, a diagram in which the horizontal axis shows, as a fluidic parameter, the height of the container 8 in relation to a reference level, in particular the aforementioned floor. By way of example, it is possible to determine the pressure in the irrigation line of the irrigation apparatus 6 on the basis of this height and/or, in particular, on the basis of further parameters. Shown on the vertical axis of this diagram is the pressure in the aspiration line of the aspiration apparatus 7 as a further fluidic parameter. The diagram shows a characteristic line I. This characteristic line I characterizes information about a stable and an unstable state obtained during a preparation phase for a specific eye 2 to be treated. Here, the characteristic line I characterizes those points at which value pairs of the fluidic parameters are present, as were set as per FIG. 3B in an influence state, and at which the lens 23 and the capsular bag 31 have adopted the state as per FIG. 3D with an area ratio of the area A1 to the area A3 of 1 or of substantially 1 and, in this respect, there is no corresponding overshoot from the state in FIG. 3C beyond the relative reference position R to the cornea if a break of the occlusion is produced. On the basis of this characteristic line I and consequently on the basis of the characteristic fields thereabove and therebelow, it is possible to clearly identify those fluidic parameter settings which are advantageous or disadvantageous during the phacoemulsification of this eye 2 to be treated. In particular, this can be seen in respect of a stable state of this eye 2 to be treated during phacoemulsification, when an occlusion occurs or when a break of an occlusion occurs.

Figure 5:
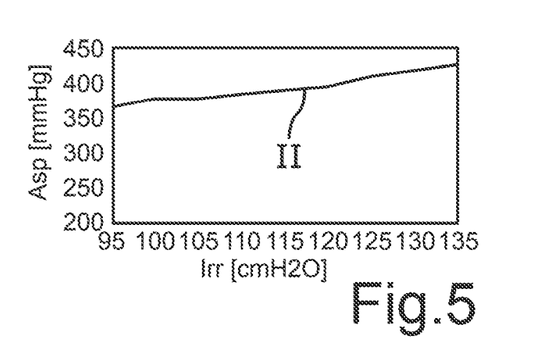

FIG. 5 shows a corresponding diagram as in FIG. 4, but for a different eye than in FIG. 4. A characteristic line II shown here therefore deviates from the characteristic line I in FIG. 4.

The diagrams as per FIG. 4 and FIG. 5 can likewise be displayed on the output unit 4a of the ophthalmic surgical system 1 in an advantageous embodiment.

The characteristic lines I and II can each be produced by determining a multiplicity of value pairs of these fluidic parameters, as explained above. However, it is also possible to only determine a few such value pairs, for example at least two such value pairs, and the characteristic line could be produced by interpolation, for example.

In particular, the ophthalmic surgical system 1, in particular the control apparatus 18, can have a computer program product comprising commands which, when the computer program product is stored on the control unit 21, are able to carry out the steps of the aforementioned method. In particular, the computer program product can be stored on a computer-readable medium, such as a hard drive. However, this computer program product could also be stored in a cloud, for example.

A further aspect of the invention relates to the use of the control apparatus 18. In particular, the control apparatus 18 is used when controlling the fluidic apparatus 5 of the ophthalmic surgical system 1, in particular when controlling fluidic parameters of a fluid of the fluidic apparatus 5, in particular of the irrigation fluid and/or of the aspiration fluid, during phacoemulsification.

It is understood that the foregoing description is that of the preferred embodiments of the invention and that various changes and modifications may be made thereto without departing from the spirit and scope of the invention as defined in the appended claims.

What is claimed is:

1. A control apparatus for an ophthalmic surgical system, the control apparatus comprising:
   a receiver module for receiving a signal containing at least a geometric size of a pupil of an eye to be treated at least at a first time point during a surgical procedure on the eye to which fluid is or has been supplied to and/or removed from the eye to be treated on a basis of set values of fluidic parameters of a fluidic apparatus of said ophthalmic surgical system;
   an evaluation unit configured to compare said signal to a geometric reference size of said pupil;
   an output module with which an output signal of said evaluation unit is outputted, said output signal of said evaluation unit containing information as to the geometric size of said pupil and/or information as to the comparison of the geometric size of said pupil contained in said signal to said geometric reference size of said pupil;
   said output module being configured to output said output signal of said evaluation unit;
   wherein said set values of the fluidic parameters include a first set of values;
   wherein said signal contains at least the geometric size of the pupil of the eye to be treated at least at a first preparation time, at which the fluid is or has been supplied to and/or removed from the eye to be treated on a basis of the first set of values of the fluidic parameters of said fluidic apparatus of the ophthalmic surgical system during a preparation phase prior to the surgical procedure; and, said receiver module receives a further signal containing at least a further geometric size of the pupil of the eye to be treated at least at a second preparation time following said first preparation time, during the preparation phase, prior to which an artificial occlusion was produced in the eye and/or prior to which an artificial breakthrough of an occlusion in the eye was produced; and, said evaluation unit is configured to evaluate said signal with the geometric size of the pupil at the first preparation time and said further signal with the further geometric size at the second preparation time; and, wherein an actual ratio of the geometric size of the pupil and the further geometric size of the pupil can be determined via said evaluation unit, wherein the actual ratio can be compared to an intended ratio of the geometric size of the pupil and the further geometric size of the pupil by way of said evaluation unit and, on a basis of the comparison of the actual ratio to the intended ratio, said evaluation unit determines whether the first set of values of the fluidic parameters at the first preparation time allows setting of a specific position setting of a lens in the eye to be treated toward a relative reference position, which is specified by the first set of values of the fluidic parameters at the first preparation time, following a breakthrough of the occlusion, wherein the specific position setting, starting from a relative position of the lens at a time of the occlusion prior to the breakthrough of said occlusion, to the relative position is implemented without an overshoot or without an overshoot beyond the relative position that is greater than a tolerance value.

2. The control apparatus of claim 1, further comprising a control unit and an output unit; and, said output module is configured to output said output signal of said evaluation unit to said control unit and/or said output unit.

3. The control apparatus of claim 2, wherein said output module is configured to output said output signal of said evaluation unit to said output unit of said ophthalmic surgical system for a user on said output unit.

4. The control apparatus of claim 3, wherein:

at least one of said signal and a second signal received by said receiver module contains at least one geometric size of a further eye part of the eye, differing from the pupil, of the eye to be treated at the first time point during the surgical procedure on the eye, at which the fluid is or has been supplied to and/or removed from the eye to be treated on the basis of the set values of the fluidic parameters of said fluidic apparatus of the ophthalmic surgical system;

said evaluation unit is configured to compare the at least one of said signal and said second signal with the geometric size of the further eye part at the first time point during the surgical procedure on the eye to be compared to a geometric reference size of the further eye part; and, at least one of said output signal and a further output signal contains information in respect of the geometric size of the further eye part and/or information in respect of the comparison of the geometric size of the further eye part with the geometric reference size of the further eye part including allowing an output of the output signal or of the further output signal to said control unit of the ophthalmic surgical system and/or allowing the output of the output signal or of the further output signal on said output unit of the ophthalmic surgical system, for the user.

5. The control apparatus of claim 4, wherein:

at least one of said signal and said second signal contain the at least one geometric size of the further eye part of the eye to be treated at least at the first preparation time, at which the fluid is or has been supplied to and/or removed from the eye to be treated on the basis of the first set of values of the fluidic parameters of said fluidic apparatus of the ophthalmic surgical system during the preparation phase prior to the surgical procedure; and, said receiver module is configured to receive said second signal, wherein said second signal contains at least the geometric size of the further eye part of the eye to be treated at least at said second preparation time, following the first preparation time, during the preparation phase prior to which the artificial occlusion was produced in the eye and/or prior to which the artificial breakthrough of the occlusion in the eye was produced;

said evaluation unit is configured to evaluate said at least one of said signal and said further signal as well as said second signal containing the geometric size of the further eye part captured at the first preparation time and the second preparation time; and, the control unit with which, during the surgical procedure, including a phacoemulsification of the eye to be treated, at least one pressure and/or a volumetric flow in an irrigation line of an irrigation apparatus and/or in an aspiration line of an aspiration apparatus, of the fluid of said fluidic apparatus is adjustable on a basis of the output signal of the output module and/or a value of the pressure and/or a value of the volumetric flow is providable including on the output unit of the ophthalmic surgical system, for the user.

6. The control apparatus of claim 4, wherein at least one of: the further eye part includes at least one of a limbal ring, a cornea, a sclera or a capsular bag of the eye; and, a value of a pressure and/or a value of a volumetric flow is providable on said output unit for the user.

7. The control apparatus of claim 3, wherein the geometric size of the pupil is at least one of an area of the pupil, a change in the area of the pupil, a diameter of the pupil, a change in the diameter of the pupil, a circumference of the pupil, or a change in the circumference of the pupil.

8. The control apparatus of claim 3, wherein said output unit is a display unit configured to display at least one of the set values of the fluidic parameters, the geometric size contained in said signal, and the comparison of the geometric size to the geometric reference size.

9. The control apparatus of claim 2, further comprising: said control unit, during the surgical procedure including a phacoemulsification of the eye to be treated, being configured to adjust at least a pressure and/or a volumetric flow including in an irrigation line of an irrigation apparatus and/or in an aspiration line of an aspiration apparatus of the fluid of said fluidic apparatus in dependence upon said output signal of said output module and/or a value of the pressure and/or a value of the volumetric flow being provided at said output unit of the ophthalmic surgical system for a user.

10. The control apparatus of claim 1, further comprising said evaluation unit, with which at least one reference fluidic parameter setting during the preparation phase can be determined on a basis of the geometric size of the pupil captured at the first preparation time and the further geometric size of the pupil captured at the second preparation time, said at least one reference fluidic parameter setting being able to be set in a case of the breakthrough of the occlusion during the surgical procedure.

11. The control apparatus of claim 1, wherein said evaluation unit is configured to predetermine the geometric reference size of the pupil during the preparation phase prior to the surgical procedure.

12. The control apparatus of claim 1, wherein the evaluation unit is configured to assess the first set of values of the fluidic parameters at the first preparation time as suitable and said set values of the fluidic parameters are a reference fluidic parameter setting if the actual ratio equals 1.

13. The control apparatus of claim 1, wherein the first set of values of the fluidic parameters at the first preparation time can be stored by the evaluation unit when the actual ratio equals or substantially equals the intended ratio.

14. The control apparatus of claim 1, wherein said receiver module is configured to receive a plurality of signals, each containing one geometric size of the pupil at a plurality of preparation times, following the breakthrough of the occlusion up to a standstill of a movement of a capsular bag and the lens of the eye, wherein said receiver module and/or said evaluation unit allow said plurality of signals to be analysed for a smallest value signal which has a smallest value of the geometric size of the pupil, wherein said smallest value signal can be set as said further signal with the further geometric size at the second preparation time.

15. The control apparatus of claim 1, wherein the evaluation unit allows geometric sizes of the pupil, which are received no further apart than 500 ms in time, to be compared to one another.

16. The control apparatus of claim 1, wherein the geometric size of the pupil is at least one of an area of the pupil, a change in the area of the pupil, a diameter of the pupil, a change in the diameter of the pupil, a circumference of the pupil, or a change in the circumference of the pupil.

17. An ophthalmic surgical system comprising:
a control apparatus;
the control apparatus including:
a receiver module for receiving a signal containing at least a geometric size of a pupil of an eye to be treated at least at a first time point during a surgical procedure on the eye to which fluid is or has been supplied to and/or removed from the eye to be treated on a basis of set values of fluidic parameters of a fluidic apparatus of said ophthalmic surgical system;
an evaluation unit configured to compare said signal to a geometric reference size of said pupil;
an output module with which an output signal of said evaluation unit is outputted, said output signal of said evaluation unit containing information as to the geometric reference size of said pupil and/or information as to the comparison of the geometric size of said pupil contained in said signal to said geometric reference size of said pupil;
said output module being configured to output said output signal of said evaluation unit;
wherein said signal contains at least the geometric size of the pupil of the eye to be treated at least at a first preparation time, at which the fluid is or has been supplied to and/or removed from the eye to be treated on a basis of a first set of values of the fluidic parameters of said fluidic apparatus of the ophthalmic surgical system during a preparation phase prior to the surgical procedure; and, said receiver module receives a further signal containing at least a further geometric size of the pupil of the eye to be treated at least at a second preparation time following said first preparation time, during the preparation phase, prior to which an artificial occlusion was produced in the eye and/or prior to which an artificial breakthrough of an occlusion in the eye was produced; and, said evaluation unit is configured to evaluate said signal with the geometric size of the pupil at the first preparation time and said further signal with the further geometric size at the second preparation time; and,
wherein an actual ratio of the geometric size of the pupil and the further geometric size of the pupil can be determined via said evaluation unit, wherein the actual ratio can be compared to an intended ratio of the geometric size of the pupil and the further geometric size of the pupil by way of said evaluation unit and, on a basis of the comparison of the actual ratio to the intended ratio, said evaluation unit determines whether the first set of values of the fluidic parameters at the first preparation time allows setting of a specific position setting of a lens in the eye to be treated toward a relative position, which is specified by the first set of values of the fluidic parameters at the first preparation time, following a breakthrough of the occlusion, wherein the specific position setting, starting from a relative position of the lens at a time of the occlusion prior to the breakthrough of said occlusion, to the relative position is implemented without an overshoot or without an overshoot beyond the relative position that is greater than a tolerance value.

18. The ophthalmic surgical system of claim 17, further comprising an optical capturing apparatus for capturing said at least one geometric size of the pupil.

19. The ophthalmic surgical system of claim 18, wherein said optical capturing apparatus is at least one camera.

20. The ophthalmic surgical system of claim 17, wherein the geometric size of the pupil is at least one of an area of the pupil, a change in the area of the pupil, a diameter of the pupil, a change in the diameter of the pupil, a circumference of the pupil, or a change in the circumference of the pupil.

* * * * *